United States Patent [19]

Mentlik

[11] 4,368,189

[45] Jan. 11, 1983

[54] COSMETIC MOISTURIZER FORMULATION

[75] Inventor: Anton A. Mentlik, Noblesville, Ind.

[73] Assignee: Eli Lilly and Company, Indianapolis, Ind.

[21] Appl. No.: 289,655

[22] Filed: Aug. 3, 1981

[51] Int. Cl.$^3$ .................. A61K 31/78; A61K 7/44
[52] U.S. Cl. .................................... 424/81; 424/60; 424/167; 424/358; 424/365
[58] Field of Search ............... 424/60, 81, 358, 365

[56] References Cited

U.S. PATENT DOCUMENTS

| 4,001,141 | 1/1977 | Kalopissis et al. | 424/358 |
| 4,143,159 | 3/1979 | Möller et al. | 424/358 |
| 4,272,519 | 6/1981 | Herrold et al. | 424/83 |
| 4,272,544 | 6/1981 | Cella et al. | 424/273 |

FOREIGN PATENT DOCUMENTS 2327087  4/1974  Fed. Rep. of Germany ...... 424/358

OTHER PUBLICATIONS

Trademark Reg. No. 1,013,311, registered 6/17/75, Skin Dynamics, Elizabeth Arden, Product Line–Everyday Moisture.
Trademark Reg. No. 977,875, registered 1/29/74.

*Primary Examiner*—Dale R. Ore
*Attorney, Agent, or Firm*—Karen B. O'Connor; Arthur R. Whale

[57] ABSTRACT

A novel cosmetic skin moisturizer formulation is described which is non-irritating and non-stinging.

1 Claim, No Drawings

COSMETIC MOISTURIZER FORMULATION

This invention relates to a novel cosmetic moisturizer formulation, which is non-irritating and non-stinging.

It is, therefore, an object of the present invention to provide a cosmetic moisturizer formulation. The moisturizer can be used in conjunction with other cosmetic formulations.

The moisturizer formulation is one of a four-component regime, which is used to treat sensitive skin. The other three components are: a cleanser, a toner, and a cream. Each of the three other components is a separate invention; the cleanser is claimed in application Ser. No. 289,657, filed Aug. 3, 1981; the toner is claimed in application Ser. No. 289,656, filed Aug. 3, 1981; and the cream is claimed in application Ser. No. 289,653, filed Aug. 3, 1981. The method of treating sensitive skin using the regime is claimed in application Ser. No. 289,658, filed Aug. 3, 1981. In addition, a cream pack formulation is claimed in application Ser. No. 289,654, filed Aug. 3, 1981.

The moisturizer formulation consists essentially of, in percent by weight:

| Ingredients | Percent |
| --- | --- |
| polyacrylic acid polymer (Carbopol No. 941) | 0.20 |
| glyoxyldiureide | 0.50 |
| polyoxyethylene (20) sorbitan fatty acid ester | 2.00 |
| cetyl alcohol (1-hexadecanol) | 2.00 |
| glyceryl monostearate | 1.25 |
| sorbitan trioleate | 5.00 |
| polyphenylmethylsiloxane | 2.50 |
| 2-ethylhexyl p-dimethylaminobenzoate | 2.00 |
| lavandin | 0.0032 |
| rosemary | 0.0066 |
| thyme | 0.0102 |
| 98% triethanolamine | 0.20 |
| squalane (2,6,10,15,19,23-hexamethyl tetracosane) | 1.50 |
| avocado oil | 2.50 |
| light mineral oil | 7.00 |
| di(2-ethylhexyl)adipate | 0.625 |
| 2-ethylhexyl stearate | 1.025 |
| 2-ethylhexyl palmitate | 0.850 |
| preservative | q.s. |
| deionized water | q.s. to 100%. |

One skilled in the cosmetic formulation art will appreciate that various preservatives can be added to the formulation in sufficient quantities. These preservatives include the esters of p-hydroxybenzoic acid, such as methyl p-hydroxybenzoate, and propyl p-hydroxybenzoate; cis-1-(3-chloroallyl)-3,5,7-triaza-1-azoniaadamantane chloride; ethylenediaminetetraacetic acid (EDTA) and salts of EDTA; imidazolidinyl urea; and the like or any combination thereof. The total amount of preservative used can vary, but usually it is from about 0.3 to about 1.0 percent.

In addition, color and essence can be included in the formulation as desired. Color additives would include both natural and artificial dyes, such as carotenoid derivatives, D+C or F,D+C colors, and the like, while essences can include any non-irritating natural and artificial oils, perfumes, and the like.

The formulation is both non-irritating and non-stinging, according to standard cosmetic testing procedures. The first procedure utilized was the Lanman-Maibach Cumulative Irritation Test, which is a 21-day patch irritation procedure as described by Dr. B. M. Lanman at the Joint Conference on Cosmetic Sciences Apr. 21-23, 1968; Washington, D.C. as further modified in Phillips, L., Steinberg M., Maibach, H., and Akers, W., *Toxicology and Applied Pharmacology* 21, 369-382 (1972). The non-stinging properties of the formulation were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197-209, May 1977.

In general, the individual ingredients used in the formulation should be of a quality or purity (such as U.S.P. or N.F.) suitable for cosmetic use.

The formulation is prepared by mixing the ingredients according to conventional methods and the preparation of this formulation is described in the following example. The example is illustrative of the formulation, but is not to be construed as limiting the invention.

EXAMPLE

Moisturizer Formulation

| Phase | Ingredient | Percent by weight |
| --- | --- | --- |
| A | deionized water | 10.00 |
|  | Carbopol No. 941 (B.F. Goodrich, polyacrylic acid polymer) | 0.20 |
| B | deionized water | 58.38 |
|  | imidazolidinyl urea | 0.30 |
|  | methylparaben (methyl p-hydroxybenzoate) | 0.25 |
|  | ethylenediaminetetraacetic acid | 0.05 |
|  | Allantoin (Sutton and Schuylkill, glyoxyldiureide) | 0.50 |
| C | Polysorbate 20 (polyoxyethylene (20) sorbitan fatty acid ester) | 2.00 |
| D | cetyl alcohol (1-hexadecanol) | 2.00 |
|  | Cerasynt SD (Van Dyk and Co., neutral, non-emulsifying glyceryl monostearate) | 1.25 |
|  | sorbitan trioleate | 5.00 |
|  | Robane (Robeco, squalane) | 1.50 |
|  | avocado oil | 2.50 |
|  | light mineral oil | 7.00 |
|  | Wickenol 163 (Wickhen Products, di(2-ethylhexyl)adipate-25%; 2-ethylhexyl stearate-41%; 2-ethylhexyl palmitate-34%) | 2.50 |
|  | Silicone Fluid No. 556 (Dow Corning, polyphenylmethylsiloxane) | 2.50 |
|  | Escalol 507 (Van Dyk and Co., 2-ethylhexyl p-dimethylaminobenzoate) | 2.00 |
|  | propylparaben (propyl p-hydroxybenzoate) | 0.15 |
| E | deionized water | 1.00 |
|  | Dowicil 200 (Dow Chemical, cis-1-(3-chloroallyl)-3,5,7-triaza-1-azoniaadamantane chloride) | 0.20 |
| F | lavandin | 0.0032 |
|  | rosemary | 0.0066 |
|  | thyme | 0.0102 |
| G | deionized water | 0.50 |
|  | 98% triethanolamine | 0.20 |

Procedure

Phase A is prepared one day before batch manufacture. The Carbopol is dispersed in the deionized water with high shear using a propeller mixer. The phase is stirred until completely hydrated and allowed to stand overnight. Phase A is stirred before added to Phase BCD.

All of the ingredients of Phase B were dissolved in the deionized water in a jacketed tank equipped with a homomixer and a sidesweep. Phase B is heated to about 75°-80° C. and then Phase C is added. The temperature of Phase BC is maintained at about 75°-80° C. (Phase BC may be cloudy or hazy).

In a jacketed tank equipped with a propeller mixer, the ingredients of Phase D are melted and mixed together. Then phase D is heated to about 75°-80° C., making sure that all the waxes are melted and the propylparaben dissolved.

Phase D is added to Phase BC and then homomixed and sideswept for 20 minutes. The temperature of Phase BCD is maintained at about 75°-80° C. The mixture is then cooled to about 40°-45° C. The homomixing is discontinued and Phase A is added slowly while mixing with the sidesweep.

Phase E is prepared by dissolving the Dowicil in the deionized water, then Phase E is added to Phase ABCD when Phase ABCD is homogeneous. After Phase ABCDE is homogeneous, Phase F is added.

Phase G is prepared by dissolving the triethanolamine in the deionized water. Then Phase G is added to Phase ABCDEF after Phase ABCDEF is homogeneous. Mixing is continued and then Phase ABCDEFG is cooled to about 25°-30° C.

I claim:

1. A cosmetic moisturizer formulation consisting essentially of, in percent by weight:

| Ingredients | Percent |
| --- | --- |
| polyacrylic acid polymer (Carbopol No. 941) | 0.20 |
| glyoxyldiureide | 0.50 |
| polyoxyethylene (20) sorbitan fatty acid ester | 2.00 |
| cetyl alcohol (1-hexadecanol) | 2.00 |
| glyceryl monostearate | 1.25 |
| sorbitan trioleate | 5.00 |
| polyphenylmethylsiloxane | 2.50 |
| 2-ethylhexyl p-dimethylaminobenzoate | 2.00 |
| lavandin | 0.0032 |
| rosemary | 0.0066 |
| thyme | 0.0102 |
| 98% triethanolamine | 0.20 |
| squalane (2,6,10,15,19,23-hexamethyl tetracosane) | 1.50 |
| avocado oil | 2.50 |
| light mineral oil | 7.00 |
| di(2-ethylhexyl)adipate | 0.625 |
| 2-ethylhexyl stearate | 1.025 |
| 2-ethylhexyl palmitate | 0.850 |
| preservative | q.s. |
| deionized water | q.s. to 100%. |

* * * * *